(12) United States Patent
Atala

(10) Patent No.: US 6,753,181 B2
(45) Date of Patent: *Jun. 22, 2004

(54) METHODS AND COMPOSITIONS FOR ORGAN DECELLULARIZATION

(75) Inventor: Anthony Atala, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 300 days.

This patent is subject to a terminal disclaimer.

(21) Appl. No.: 10/091,665

(22) Filed: Mar. 5, 2002

(65) Prior Publication Data

US 2002/0102727 A1 Aug. 1, 2002

Related U.S. Application Data

(63) Continuation of application No. 09/474,678, filed on Dec. 29, 1999, now Pat. No. 6,376,244.

(51) Int. Cl.[7] ................................................ L12N 5/00
(52) U.S. Cl. ........................ 435/376; 435/1.1; 435/379; 435/395; 530/536
(58) Field of Search ........................ 435/376, 1.1, 379, 435/395; 530/536

(56) References Cited

U.S. PATENT DOCUMENTS

| | | |
|---|---|---|
| 4,458,678 A | 7/1984 | Yannas et al. |
| 4,520,821 A | 6/1985 | Schmidt et al. |
| 4,801,299 A | 1/1989 | Brendel et al. |
| 4,963,489 A | 10/1990 | Naughton et al. |
| 5,032,508 A | 7/1991 | Naughton et al. |
| 5,160,490 A | 11/1992 | Naughton et al. |
| 5,192,312 A | 3/1993 | Orton |
| 5,443,950 A | 8/1995 | Naughton et al. |
| 5,516,680 A | 5/1996 | Naughton et al. |
| 5,567,612 A | 10/1996 | Vacanti et al. |
| 5,613,982 A | 3/1997 | Goldstein |
| 5,632,778 A | 5/1997 | Goldstein |
| 5,753,267 A | 5/1998 | Badylak et al. |
| 5,759,830 A | 6/1998 | Vacanti et al. |
| 5,762,966 A | 6/1998 | Knapp, Jr. et al. |
| 5,770,193 A | 6/1998 | Vacanti et al. |
| 5,770,417 A | 6/1998 | Vacanti et al. |
| 5,843,182 A | 12/1998 | Goldstein |
| 5,851,833 A | 12/1998 | Atala |
| 5,855,610 A | 1/1999 | Vacanti et al. |
| 5,858,721 A | 1/1999 | Naughton et al. |
| 5,863,531 A | 1/1999 | Naughton et al. |
| 5,866,414 A | 2/1999 | Badylak et al. |
| 5,899,936 A | 5/1999 | Goldstein |
| 5,916,265 A | 6/1999 | Hu |
| 5,962,325 A | 10/1999 | Naughton et al. |
| 6,376,244 B1 * | 4/2002 | Atala |

FOREIGN PATENT DOCUMENTS

WO        8803785        6/1988

OTHER PUBLICATIONS

U.S. patent application Ser. No. 09/474,525, Atala, filed Dec. 1999.
U.S. patent application Ser. No. 09/474,524, Atala, filed Dec. 1999.
U.S. patent application Ser. No. 09/474,391, Atala, filed Dec. 1999.
da Silva, et al., "An In Vivo Model to Quantify Motor abd Sensory Peripheral Nerve Regeneration Using Bioresorbable Nerve Guide Tubes," *Brain Research*, vol. 342, 1985, pp 307–315.
Michalopoulos, et al., "Primary Culture of Parenchymal Liver Cells on Collagen Membranes," *Experimental Cell Research*, vol. 94, 1975, pp 70–78.
Mooney, et al., "Tissue Engineering Using Cells and Synthetic Polymers," *Transplantation Reviews*, vol. 7, No. 3, Jul. 1993, pp 153–162.
Rosen et al., "Bioerodible Polyanhydrides for Controlled Drug Delivery," *Biomaterials*, vol. 4, Apr. 1983, pp 131–133.
Schmidt, "Acellular Vascular Tissues: Natural Biomaterials for Tissue Repair and Tissue Engineering," *Biomaterials*, vol. 21, 2000, pp 2215–2231.
Walton et al., "Tissue Engineering of Biomaterials for Composite Reconstruction: An Experimental Model," *Annals of Plastic Sugery*, vol. 30, No. 2, Feb. 1993, pp 105–110.
International Search Report, PCT/US00/33782, Apr. 5, 2001.

* cited by examiner

*Primary Examiner*—Leon B. Lankford, Jr.
(74) *Attorney, Agent, or Firm*—Thomas J. Engellenner; Jasbir Sagoo; Nutter McClennen & Fish LLP

(57) ABSTRACT

The invention is directed to methods for producing a decellularized organ or part of an organ. A decellularized organ is produced using an isolated organ mechanically agitated to remove cellular membranes surrounding the isolated organ without destroying the interstitial structure of the organ. After the cellular membrane is removed, the isolated organ is exposed to a solubilizing fluid that extracts cellular material without dissolving the interstitial structure of the organ. A washing fluid is used to remove the solubilized components, leaving behind a decellularized organ.

26 Claims, No Drawings

METHODS AND COMPOSITIONS FOR ORGAN DECELLULARIZATION

REFERENCE TO RELATED APPLICATIONS

This application is a continuation of U.S. patent application Ser. No. 09/474,678, filed Dec. 29, 1999, now U.S. Pat. No. 6,376,244 the content of which are expressly incorporated by reference.

BACKGROUND OF THE INVENTION

The technical field of this invention relates to methods of decellularizing an isolated organ or part of an organ, by mechanically agitating the isolated organ with a fluid that removes the cellular membrane surrounding the isolated organ, and with a fluid that solubilizes the cytoplasmic and nuclear components of the isolated organ.

Techniques for restoring structure and function to damaged organs or tissue are used routinely in the area of reconstructive surgery. For example, artificial materials for replacing limbs and teeth. (See e.g. Paul (1999), *J. Biomech*, 32: 381–393; Fletchall, et al., (1992) *J. Burn Care Rehabil*, 13: 584–586 and Wilson et al., (1970) *Artif. Limbs*, 14: 53–56).

Tissue transplantation is another way of restoring function by replacing the damaged organ, and has saved the lives of many. However, problems exist when there is a transfer of biological material form one individual to another. Organ rejection is a significant risk associated with transplantation, even with a good histocompatability match. Immunosuppressive drugs such as cyclosporin and FK506 are usually given to the patient to prevent rejection. These immunosuppressive drugs however, have a narrow therapeutic window between adequate immunosuppression and toxicity. Prolonged immunosuppression can weaken the immune system, which can lead to a threat of infection. In some instances, even immunosuppression is not enough to prevent organ rejection. Another major problem of transplantation, is the availability of donor organs. In the United States alone there are about 50,000 people on transplant waiting lists, many of whom will die before an organ becomes available.

Due to these constraints, investigators are involved in the technology of producing artificial organs in vitro for in vivo transplantation. The artificial organs typically are made of living cells fabricated onto a matrix or a scaffold made of natural or manmade material. These artificial organs avoid the problems associated with rejection or destruction of the organ, especially if the subject's own tissue cells are used for reconstruction of the artificial organ. These artificial organs also avoid the problem of not having enough donor organs available because any required number of organs can be reconstructed in vitro.

Vacanti et al. have disclosed methods for culturing cells in a three-dimensional polymer-cell scaffold made of a biodegradable polymer. Organ cells are cultured within the polymer-cell scaffold which is implanted into the patient. Implants made of resorbable materials are suggested for use as temporary replacements, rather than a permanent replacement. The object of the temporary replacement is to allow the healing process to replace the resorbed material. Naughton et al. reported a three-dimensional tissue culture system in which stromal cells were laid over a polymer support system (See U.S. Pat. No. 5,863,531).

The above methods however, rely on shaping the support scaffold into the desired configuration of the organ. Shaping the matrix scaffold involves one of many procedures, such as solvent casting, compression, moulding, and leaching. These techniques do not always result in a matrix shape scaffold that is the same size as a native in vivo organ requiring replacement. A correct three-dimensional configuration is essential for the reconstructed organ to function properly in vivo. Not only is the shape required to fit into the body cavity, but the shape also creates the necessary microenvironment for the cultured cells to attach, proliferate, differentiate and in some cases, migrate through the matrix scaffold. These critical requirements can be met by the choice of the appropriate material of the scaffold and also be effected by the processing techniques. Optimal cell growth and development arises when the interstitial structure of the microenvironment resembles the interstitial structure of a natural organ.

The shaping process may have deleterious effects on the mechanical properties of scaffold, and in many cases produce scaffolds with irregular three-dimensional geometries. Additionally, many shaping techniques have limitations that prevent their use for a wide variety of polymer materials. For example, poly L-lactic acid (PLLA) dissolved in methylene chloride and cast over the mesh of polyglycolic acid (PGA) fibers is suitable for PGA, however, the choice of solvents, and the relative melting temperatures of other polymers restricts the use of this technique for other polymers. Another example includes solvent casting, which is used for a polymer that is soluble in a solvent such as chloroform. The technique uses several salt particles that are dispersed in a PLLA/chloroform solution and cast into a glass container. The salt particles utilized are insoluble in chloroform. The solvent is allowed to evaporate and residual amounts of the solvent are removed by vacuum-drying. The disadvantages of this technique is that it can only be used to produce thin wafers or membranes up to 2 mm in thickness. A three-dimensional scaffold cannot be constructed using this technique.

Due to the limitations of the shaping techniques, and due to the importance of having a scaffold with the correct three-dimensional shape, a need exists for producing a decellularized organ that has the same three-dimensional interstitial structure, shape and size as the native organ. Reconstruction of an artificial organ using a decellularized organ will produce an artificial organ that functions as well as a native organ, because it retains the same shape, size and interstitial structure which enables the deposited cells to resume a morphology and structure comparable to the native organ.

SUMMARY OF THE INVENTION

In general, the invention pertains to methods of producing decellularized organs, using an isolated organ or a part of an organ and a series of extractions that removes the cell membrane surrounding the organ, or part of an organ, and the cytoplasmic and nuclear components of the isolated organ, or part of an organ.

Accordingly, in one aspect, the invention provides a method for producing a decellularized organ comprising:
   mechanically agitating an isolated organ to disrupt cell membranes without destroying the interstitial structure of the organ;
   treating the isolated organ in a solubilizing fluid at a concentration effective to extract cellular material from the organ without dissolving the interstitial structure of the organ; and
   washing the isolated organ in a washing fluid to remove cellular debris without removing the interstitial structure of the organ until the isolated organ is substantially free of cellular material, to thereby produce a decellularized organ.

The method can further comprise equilibrating the decellularized organ in an equilibrating fluid. The equilibrating fluid can be selected from the group consisting of distilled water, physiological buffer and culture medium. The method can further comprise drying the decellularized organ. The dried decellularized organ can be stored at a suitable temperature, or equilibrated in a physiological buffer prior to use.

In one embodiment, the step of mechanically agitating the isolated organ further comprises placing the isolated organ in a stirring vessel having a paddle which rotates at a speed ranging from about 50 revolutions per minute (rpm) to about 150 rpm.

In one embodiment, the step of mechanically agitating the isolated organ occurs in a fluid selected from the group consisting of distilled water, physiological buffer and culture medium.

In one embodiment, the step of treating the isolated organ in the solubilizing fluid also occurs in a stirring vessel. In a preferred embodiment, the solubilizing fluid is an alkaline solution having a detergent. In a more preferred embodiment, the alkaline solution is selected from the group consisting of sulphates, acetates, carbonates, biocarbonates and hydroxides, and a detergent is selected from the group consisting of Triton X-100, Triton N-101, Triton X-114, Triton X-405, Triton X-705, and Triton DF-16, monolaurate (Tween 20), monopalmitate (Tween 40), monooleate (Tween 80), polyoxyethylene-23-lauryl ether (Brij 35), polyoxyethylene ether W-1 (Polyox), sodium cholate, deoxycholates, CHAPS, saponin, n-Decyl β-D-glucopuranoside, n-heptyl β-D glucopyranoside, n-Octyl α-D-glucopyranoside and Nonidet P-40. In the most preferred embodiment, the solubilizing agent is an ammonium hydroxide solution having Triton X-100.

In one embodiment, the step of washing the isolated organ also occurs in a stirring vessel. The washing fluid can be selected from the group consisting of distilled water, physiological buffer and culture medium.

In another aspect, the invention features a method for producing a decellularized kidney comprising:

mechanically agitating an isolated kidney in distilled water to disrupt cell membranes without destroying the interstitial structure of the kidney;

treating the isolated kidney in an alkaline solution having a detergent at a concentration effective to extract cellular material without dissolving the interstitial structure of the kidney;

washing the isolated kidney in distilled water to remove cellular debris without removing the interstitial structure of the kidney until the kidney is substantially free of the cellular material, to thereby produce a decellularized kidney.

In a preferred embodiment, the method further comprises equilibrating the decellularized kidney in a phosphate buffered solution. In another embodiment, the method further comprises drying the decellularized kidney. Embodiments for mechanically agitating a decellularized organ are described above and are reiterated here. In another preferred embodiment, the step of washing further comprises rotating the isolated kidney in distilled water in a stirring vessel.

DETAILED DESCRIPTION

So that the invention may more readily be understood, certain terms are first defined as follows:

The term "decellularized organ" as used herein refers to an organ, or part of an organ from which the entire cellular and tissue content has been removed leaving behind a complex interstitial structure. Organs are composed of various specialized tissues. The specialized tissue structures of an organ are the parenchyma tissue, and they provide the specific function associated with the organ. Most organs also have a framework composed of unspecialized connective tissue which supports the parenchyma tissue. The process of decellularization removes the parenchyma tissue, leaving behind the three-dimensional interstitial structure of connective tissue, primarily composed of collagen. The interstitial structure has the same shape and size as the native organ, providing the supportive framework that allows cells to attach to, and grow on it. Decellularized organs can be rigid, or semi-rigid, having an ability to alter their shapes. Examples of decellularized organs include, but are not limited to the heart, kidney, liver, pancreas, spleen, bladder, ureter and urethra.

The term "isolated organ" as used herein refers to an organ that has been removed from a mammal. Suitable mammals include humans, primates, dogs, cats, mice, rats, cows, horses, pigs, goats and sheep. The term "isolated organ" also includes an organ removed from the subject requiring an artificial reconstructed organ. Suitable organs can be any organ, or part of organ, required for replacement in a subject. Examples include but are not limited to the heart, kidney, liver, pancreas, spleen, bladder, ureter and urethra.

The present invention provides methods for decellularizing organs. Decellularization of organs comprises removing the nuclear and cellular components of an isolated organ, or a part of an organ, leaving behind an interstitial structure having the same size and shape of a native organ.

Various aspects of the invention are described in further detail in the following subsections:

I Isolation of Natural Organs

An organ, or a part of an organ, can be isolated from the subject requiring an artificial reconstructed organ. For example, a diseased organ in a subject can be removed and decellularized, as long as the disease effects the parenchyma tissue of the organ, but does not harm the connective tissue, e.g., tissue necrosis. The diseased organ can be removed from the subject and decellularized as described in Example 1 and in Section II. The decellularized organ, or a part of the organ, can be used as a three-dimensional scaffold to reconstruct an artificial organ. An allogenic artificial organ can be reconstructed using the subject's own decellularized organ as a scaffold and using a population of cells derived from the subject's own tissue. For example, cells populations derived from the subject's skin, liver, pancreas, arteries, veins, umbilical cord, and placental tissues.

A xenogenic artificial organ can be reconstructed using the subject's own decellularized organ as a scaffold, and using cell populations derived from a mammalian species that are different from the subject. For example the different cell populations can be derived from mammals such as primates, dogs, cats, mice, rats, cows, horses, pigs, goats and sheep.

An organ, or part of an organ, can also be derived from a human cadaver, or from mammalian species that are different from the subject, such as organs from primates, dogs, cats, mice, rats, cows, horses, pigs, goats and sheep. Standard methods for isolation of a target organ are well known to the skilled artisan and can be used to isolate the organ.

II Decellularization of Organs

An isolated organ, or part of an organ, can be decellularized by removing the entire cellular material (e.g., nuclear and cytoplasmic components) from the organ, as described in Example 1. The decellularization process comprises a series of sequential extractions. One key feature of this extraction process is that harsh extraction, that may disturb or destroy the complex interstitial structure of the biostructure, be avoided. The first step involves removal of cellular debris and cell membranes surrounding the isolated organ, or part of an organ. This is followed by solubilization of the nuclear and cytoplasmic components of the isolated organ, or part of the organ using a solubilizing fluid, leaving behind a three-dimensional interstitial structure.

The organ can be decellularized by removing the cell membrane surrounding the organ using mechanical agitation methods. Mechanical agitation methods must be sufficient to disrupt the cellular membrane. However, the mechanical agitation methods should not damage or destroy the three-dimensional interstitial structure of the isolated organ.

In one embodiment, the mechanical agitation method involves using a magnetic stir plate and a paddle, e.g., a magnetic stirrer. The isolated organ, or part of an organ, is placed in a container with a suitable volume of fluid and stirred on the magnetic stir plate at a suitable speed. A suitable speed for stirring the isolated organ will depend on the size of the isolated organ. For example. Rotation at about 50 revolutions per minute (rpm) to about 150 rpm. A large organ will require a faster speed, compared with a smaller organ. The volume of fluid in which the isolated organ is placed in will also depend on the size of the isolated organ. Suitable fluids depend on which layer of the organ is being removed and are described in more detail.

In another embodiment, the mechanical agitation method involves using a mechanical rotator. The organ, or part of the organ, is placed in a sealed container with a suitable volume of fluid. The container is placed on the rotator platform and rotated at 360°. The speed of rotation, and the volume of fluid will depend on the size of the isolated organ.

In another embodiment, the mechanical agitation method involves using a low profile roller. The organ, or part of the organ, is placed in a sealed container with a suitable volume of fluid. The container is placed on the roller platform and rolled at a selected speed in a suitable volume of fluid depending o the size of the organ. One skilled in the art will appreciate that these mechanical agitation devices can be commercially obtained from, for example, Sigma Co.

In other embodiments, the agitation can also include placing the isolated organ in a closed container e.g., a self-sealing polyethylene bag, a plastic beaker. The container can be placed in a sonicating waterbath, and exposed to sonication methods that include, but are not limited to, acoustic horns, piezo-electric crystals, or any other method of generating stable sound waves, for example, with sonication probes. The sonication should be conducted at a frequency that selectively removes cell membranes and/or cellular material, without destroying the interstitial structure. Suitable sonication frequencies will depend on the size and the type of the isolated organ being decellularized. Typical sonicaton frequencies are between 40 kHz to 50 kHz. However, a fairly wide range of frequencies from subaudio to ultrasound (between about 7 Hz to 40 MHz, preferably between 7 Hz and 20 MHz) would be expected to give sound-enhanced tissue dissociation. Variations in the type of sonication are also contemplated in the invention and include pulsing versus continuous sonication. Power levels for sonication source is between $10^{-4}$ and about 10 watts/ $cm^2$ (See Biological Effects of Ultrasound: Mechanisms and Clinical Implications, National Council on Radiation Protection and Measurements (NCRP) Report No. 74, NCRP Scientific Committee No. 66: Wesley L. Nyborg, chairman; 1983; NCRP, Bethesda, Md.

The decellularization method requires the sequential removal of components of the isolated organ, or part of the organ. The first step involves mechanically agitating the isolated organ, or part of the organ, until the cell membrane surrounding the organ is disrupted and a cellular debris around the organ has been removed. This step can involve using a membrane striping fluid that is capable of removing the cellular membranes surrounding the isolated organ, or part of an organ. Examples of a membrane striping fluid include, but are not limited to, distilled water, physiological buffer and culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like. The membrane striping fluid should be capable of removing the cellular membrane surrounding the isolated organ, particularly when mechanically agitated. In a preferred embodiment, the membrane striping fluid is distilled water.

After the cell membrane has been removed, the second step involves removal of cellular material, for example native tissue cells and the nuclear and cytoplasmic components of the organ, or part of an organ. Cellular material can be removed, for example, by mechanical agitation of the isolated organ, or part of an organ in a solubilizing fluid. The solubilizing fluid is an alkaline solution having a detergent. During this step, the cellular material of the isolated organ is solubilized without dissolving the interstitial structure of the organ.

The cytoplasmic component, consisting of the dense cytoplasmic filament networks, intercellular complexes and apical microcellular structures, can be solubilized using an alkaline solution, such as, ammonium hydroxide. Other alkaline solution consisting of ammonium salts or their derivatives may also be used to solubilize the cytoskeletal components. Examples of other suitable ammonium solutions include, but are not limited to, ammonium sulphate, ammonium acetate, ammonium bicarbonate, ammonium carbonate and ammonium hydroxide. In a preferred embodiment, ammonium hydroxide is used. Other alkaline solutions also include, but are not limited to, sulphates, acetates, hydroxides and carbonates of calcium, lithium, sodium and potassium.

The concentration of the alkaline solutions, e.g., ammonium hydroxide, may be altered depending on the type of organ being decellularized. For example, for delicate tissues, e.g., blood vessels, the concentration of the detergent should be decreased. Preferred concentrations ranges can be from about 0.006% (w/v) to about 1.6% (w/v). More preferably, about 0.0125% (w/v) to about 0.8% (w/v). More preferably, about, 0.025% (w/v) to about 0.04% (w/v). More preferably about 0.05% (w/v) to about 0.25% (w/v). More preferably, about 0.05% (w/v) to about 0.1% (w/v). Even more preferably, about 0.0125% (w/v) to about 0.1% (w/v).

To solubilize the nuclear components, non-ionic detergents or surfactants can be used in an alkaline solution. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxyethylene-23-lauryl ether (Brij 35), polyoxyethylene ether W-1 (Polyox), and the like, sodium cholate, deoxycholates, CHAPS, saponin, n-Decyl β-D-glucopuranoside, n-heptyl β-D glucopyranoside, n-Octyl α-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem, Hoechst Celanese Corp., 1987. In one preferred embodiment, the non-ionic surfactant is the Triton series, preferably, Triton X-100.

The concentration of the non-ionic detergent may be altered depending on the type of organ being decellularized. For example, for delicate tissues, e.g., blood vessels, the concentration of the detergent should be decreased. Preferred concentrations ranges of the non-ionic detergent can be from about 0.00625% (w/v) to about 2.0% (w/v). More preferably, about 0.125% (w/v) to about 1.0% (w/v). Even more preferably, about 0.25% (w/v) to about 0.5% (w/v). The skilled artisan will appreciate that any combination of alkaline solution with any combination of a detergent, at the above concentration ranges, can be used depending on the size and type of organ being decellularized. In other embodiments, one or more detergents can be used in an alkaline solution.

After solubilizing the cytoplasmic and nuclear components of the isolated organ, or part of an organ, the next step in the sequential extraction involves removal of the solubilized components by mechanically agitating the isolated organ in a washing fluid. Removal of the cytoplasmic and nuclear components leaves behind a three-dimensional connective tissue interstitial structure having the same shape and size as the native organ. Examples of a washing fluid include, but are not limited to, distilled water, physiological buffer and culture medium. Examples of suitable buffers and culture media are described Supra. In a preferred embodiment, the washing fluid is distilled water.

After removing the solubilized cytoplasmic and nuclear components, the next step of the sequential extraction can involve equilibrating the decellularized organ in an equilibrating fluid. Examples of an equilibrating fluid include, but are not limited to, distilled water, physiological buffer and culture medium. Examples of suitable buffers and culture media are described Supra.

The decellularized organ can be dried for long term storage. Methods for drying the decellularized organ include freeze-drying or lyophilizing the organ to remove residual fluid. The lyophilized decellularized organ can be stored at a suitable temperature until required for use. Prior to use, the decellularized organ can be equilibrated in suitable physiological buffer or cell culture medium. Examples of suitable buffers and culture media are described Supra.

III Reconstructing Artificial Organs Using a Decellularized Organ

The invention provides a method of reconstructing an artificial organ using a decellularized organ as a scaffold. This decellularized organ supports the maturation, differentiation, and segregation of in vitro cultured cell populations to form components of adult tissues analogous to counterparts found in vivo.

The decellularized organ produced by the method of the invention can be used as a three-dimensional scaffold to reconstruct an artificial organ. Either allogenic or xenogenic cell populations can be used to reconstruct the artificial organ. Methods for the isolation and culture of cells used to reconstruct an artificial organ are discussed by Freshney, Culture of Animal Cells. A Manual of Basic Technique, 2d Ed., A. R. Liss, Inc., New York, 1987, Ch. 9, pp. 107–126. Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the organ, the use of grinders, blenders, sieves, homogenizers, pressure cells, or insonators to name but a few.

Preferred cell types include, but are not limited to, kidney cells, urothelial cells, mesenchymal cells, especially smooth or skeletal muscle cells, myocytes (muscle stem cells), fibroblasts, chondrocytes, adipocytes, fibromyoblasts, and ectodermal cells, including dulctile and skin cells, hepatocytes, Islet cells, cells present in the intestine, and other parenchymous cells, osteoblasts and other cells forming bone or cartilage.

Isolated cells can be cultured in vitro to increase the number of cells available for infusion into the three-dimensional scaffold. The use of allogenic cells, and more preferably autologous cells, is preferred to prevent tissue rejection. However, if an immunological response does occur in the subject after implantation of the reconstructed artificial organ, the subject may be treated with immunosuppressive agents such as, cyclosporin or FK506, to reduce the likelihood of rejection.

It is important to recreate, in culture, the cellular microenvironment found in vivo for a particular organ being reconstructed. The invention provides a method in which a decellularized organ is used as a three-dimensional scaffold to reconstruct an artificial organ. By using a decellularized organ, the connective tissue interstitial structure is retained. This enables perfused cultured cell populations to attach to the three-dimensional scaffold. Retaining a three-dimensional interstitial structure that is the same as an in vivo organ, creates the optimum environment for cell-cell interactions, development and differentiation of cell populations.

The decellularized organ can be pre-treated prior to perfusion of cultured endothelial cells in order to enhance the attachment of cultured cell populations to the decellularized organ. For example, the decellularized organ could be treated with, for example, collagens, elastic fibers, reticular fibers, glycoproteins, glycosaminoglycans (e.g., heparan sulfate, chondroitin-4-sulfate, chondroitin-6-sulfate, dermatan sulfate, keratin sulfate, etc.).

Cultured cell populations, e.g., endothelial cells, can be perfused into the decellularized organ using needles placed in localized positions of the decellularized organ. A decellularized organ perfused with a cell population is referred to as a "perfused organ". After perfusion of a cell population, e.g., endothelial cells, the perfused organ should be incubated in an appropriate nutrient medium. Many commercially available media such as RPMI 1640, Fisher's, Iscove's, McCoy's, Dulbecco's medium, and the like, may be suitable for use. In addition, the culture medium should be changed periodically to remove the used media, depopulate released cells, and add fresh media. During the incubation period, the endothelial cells will grow in the perfused organ to produce an endothelial tissue layer.

Additional populations of cultured cells, such as parenchymal cells, can be perfused onto the endothelial tissue layer. Parenchyma cells perfused onto the endothelial tissue can be incubated to allow the cells to adhere to the endothelial tissue layer. The parenchyma cells can be cultured in vitro in culture medium to allow the cells to grow and develop until the cells resemble a morphology and structure similar to the that of the native tissue. Growth of parenchyma cells on the endothelial tissue layer results in the differentiation of parenchyma cells into the appropriate neomorphic organ structures.

Alternatively, after perfusing the decellularized organ, the perfused organ can be implanted in vivo without prior in vitro culturing of the parenchyma cells. The parenchyma cells chosen for perfusion will depend upon the organ being reconstructed. For example, reconstruction of a kidney will involve infusing cultured endothelial cells into a decellularized kidney scaffold. The perfused kidney scaffold is cultured until the cells develop into endothelial tissue layer comprising a primitive vascular system. The endothelial tissue can then be perfused with a population of cultured kidney cells and the perfused kidney, cultured in vitro until the kidney cells begin to differentiate to form nephron structures. One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1
Preparation of a Decellularized Kidney

The following method describes a process for removing the entire cellular content of an organ or tissue without destroying the complex three-dimensional interstitial structure of the organ or tissue. A kidney, was surgically removed from a C7 black mouse using standard techniques for tissue removal. The kidney was placed in a flask containing a suitable volume of distilled water to cover the isolated kidney. A magnetic stir plate and magnetic stirrer were used to rotate the isolated kidney in the distilled water at a suitable speed of about 95–150 rpm for 24–48 hours at 4° C. This process removes the cellular debris and cell membrane surrounding the isolated kidney.

After this first removal step, the distilled water was replaced with a 0.05% ammonium hydroxide solution containing 0.5% Triton X-100. The kidney was rotated in this solution for 72 hours at 4° C. using a magnetic stir plate and magnetic stirrer at a speed of 95–150 rpm. This alkaline solution solubilized the nuclear and cytoplasmic components of the isolated kidney. The detergent Triton X-100, was used to remove the nuclear components of the kidney, while the ammonium hydroxide solution was used to lyse the cell membrane and cytoplasmic proteins of the isolated kidney.

The isolated kidney was then washed with distilled water for 24–48 hours at 4° C. using a magnetic stir plate and magnetic stirrer at a speed of 95–150 rpm. After this washing step, removal of cellular components from the isolated kidney was confirmed by histological analysis of a small piece of the kidney. If necessary, the isolated kidney was again treated with the ammonium hydroxide solution containing Triton X-100 until the entire cellular content of the isolated kidney was removed. After removal of the solubilized components, a collagenous three-dimensional framework in the shape of the isolated kidney was produced.

This decellularized kidney was equilibrated with 1× phosphate buffer solution (PBS) by rotating the decellularized kidney overnight at 4° C. using a magnetic stir plate and magnetic stirrer. After equilibration, the decellularized kidney was lyophilized overnight under vacuum. The lyophilized kidney was sterilized for 72 hours using ethylene oxide gas. After sterilization, the decellularized kidney was either used immediately, or stored at 4° C. or at room temperature until required. Stored organs were equilibrated in the tissue culture medium overnight at 4° C. prior to seeding with cultured cells.

What is claimed is:

1. A method for producing a decellularized organ scaffold comprising:
   mechanically agitating an isolated untreated organ in membrane stripping fluid to disrupt cell membranes while maintaining the interstitial structure of the organ;
   treating the isolated organ in a solubilizing fluid at a concentration effective to extract cellular material from the organ while maintaining the interstitial structure of the organ; and
   washing the isolated organ in a washing fluid to remove cellular debris while maintaining the interstitial structure of the organ until the isolated organ is substantially free of cellular material, to thereby produce a decellularized organ scaffold.

2. The method of claim 1, further comprising equilibrating the decellularized organ scaffold in an equilibrating fluid.

3. The method of claim 2, further comprising drying the decellularized organ scaffold.

4. The method of claim 1, wherein the step of mechanically agitating the isolated organ comprises placing the isolated organ in a stirring vessel having a paddle which rotates at a speed ranging from about 50 revolutions per minute (rpm) to about 150 rpm.

5. The method of claim 1, wherein the step of mechanically agitating the isolated organ in membrane stripping fluid occurs in a non-detergent membrane stripping fluid.

6. The method of claim 5, wherein the step of mechanically agitating the isolated organ occurs in a non-detergent membrane stripping fluid selected from the group consisting of distilled water, physiological buffer and culture medium.

7. The method of claim 1, wherein the step of treating the isolated organ in the solubilizing fluid also occurs in a stirring vessel.

8. The method of claim 7, wherein the step of treating comprises using a solubilizing fluid that is an alkaline solution having a detergent.

9. The method of claim 8, wherein the step of treating comprises treating the isolated organ in an alkaline solution selected from the group consisting of sulphates, acetates, carbonates, bicarbonates and hydroxides, and a detergent selected from the group consisting of Triton X-100, Triton N-101, Triton X-114, Triton X-405, Triton X-705, and Triton DF-16, monolaurate (Tween 20), monopalmitate (Tween 40), monooleate (Tween 80), polyoxethylene-23-lauryl ether (Brij 35), polyoxyethylene ether W-1 (Polyox), sodium cholate, deoxycholates, CHAPS, saponin, n-Decyl β-D-glucopuranoside, n-heptyl β-D glucopyranoside, n-Octyl α-D-glucopyranoside and Nonidet P-40.

10. The method of claim 9, wherein the step of treating comprises treating the isolated organ in an ammonium hydroxide solution having Triton X-100.

11. The method of claim 1, wherein the step washing the isolated organ also occurs in a stirring vessel.

12. The method of claim 1, wherein the step of washing comprises washing the isolated organ in a washing fluid selected from the group consisting of distilled water, physiological buffer and culture medium.

13. The method of claim 2, wherein the step of equilibrating comprises equilibrating the decellularized organ scaffold in an equilibrating fluid selected from the group consisting of distilled water, physiological buffer and culture medium.

14. A method for producing a decellularized blood vessel scaffold comprising:
  mechanically agitating an isolated untreated blood vessel in membrane stripping fluid to disrupt the outer part of the blood vessel while maintaining the interstitial structure of the blood vessel;
  treating the isolated blood vessel in a solubilizing fluid at a concentration effective to extract cellular material from the blood vessel while maintaining the interstitial structure of the blood vessel; and
  washing the isolated blood vessel in a washing fluid to remove cellular debris while maintaining the interstitial structure of the blood vessel until the isolated blood vessel is substantially free of cellular material, to thereby produce a decellularized blood vessel scaffold.

15. The method of claim 14, further comprising equilibrating the decellularized blood vessel scaffold in an equilibrating fluid.

16. The method of claim 15, further comprising drying the decellularized blood vessel scaffold.

17. The method of claim 14, wherein the step of mechanically agitating the isolated blood vessel comprises placing the isolated blood vessel in a stirring vessel having a paddle which rotates at a speed ranging from about 50 revolutions per minute (rpm) to about 150 rpm.

18. The method of claim 14, wherein the step of mechanically agitating the isolated blood vessel in membrane stripping fluid occurs in a non-detergent membrane stripping fluid.

19. The method of claim 18, wherein the step of mechanically agitating the isolated blood vessel occurs in a non-detergent membrane stripping fluid selected from the group consisting of distilled water, physiological buffer and culture medium.

20. The method of claim 14, wherein the step of treating the isolated blood vessel in the solubilizing fluid also occurs in a stirring vessel.

21. The method of claim 20, wherein the step of treating comprises using a solubilizing fluid that is an alkaline solution having a detergent.

22. The method of claim 21, wherein the step of treating comprises treating the isolated blood vessel in an alkaline solution selected from the group consisting of sulphates, acetates, carbonates, bicarbonates and hydroxides, and a detergent selected from the group consisting of Triton X-100, Triton N-101, Triton X-114, Triton X-405, Triton X-705, and Triton DF-16, monolaurate (Tween 20), monopalmitate (Tween 40), monooleate (Tween 80), polyoxethylene-23-lauryl ether (Brij 35), polyoxyethylene ether W-1 (Polyox), sodium cholate, deoxycholates, CHAPS, saponin, n-Decyl β-D-glucopuranoside, n-heptyl β-D glucopyranoside, n-Octyl α-D-glucopyranoside and Nonidet P-40.

23. The method of claim 22, wherein the step of treating comprises treating the isolated organ in an ammonium hydroxide solution having Triton X-100.

24. The method of claim 14, wherein the step of washing the isolated blood vessel also occurs in a stirring vessel.

25. The method of claim 14, wherein the step of washing comprises washing the isolated blood vessel in a washing fluid selected from the group consisting of distilled water, physiological buffer and culture medium.

26. The method of claim 15, wherein the step of equilibrating comprises equilibrating the decellularized blood vessel scaffold in an equilibrating fluid selected from the group consisting of distilled water, physiological buffer and culture medium.

* * * * *